United States Patent
Stewart et al.

(10) Patent No.: US 9,533,949 B2
(45) Date of Patent: Jan. 3, 2017

(54) PROCESSES FOR THE PREPARATION OF 3-ALKYL INDOLES

(71) Applicant: APOTEX PHARMACHEM INC., Brantford (CA)

(72) Inventors: Craig Stewart, Milton (CA); Peter Garth Blazecka, Brantford (CA); Gamini Weeratunga, Ancaster (CA); Uma Kotipalli, Brantford (CA); Sammy Chris Duncan, Brantford (CA); Yajun Zhao, Brantford (CA)

(73) Assignee: Apotex Pharmachem Inc., Brantford, Ontario (CA)

( * ) Notice: Subject to any disclaimer, the term of this patent is extended or adjusted under 35 U.S.C. 154(b) by 0 days.

(21) Appl. No.: 14/427,926

(22) PCT Filed: Sep. 12, 2013

(86) PCT No.: PCT/CA2013/000766
§ 371 (c)(1),
(2) Date: Mar. 12, 2015

(87) PCT Pub. No.: WO2014/040164
PCT Pub. Date: Mar. 20, 2014

(65) Prior Publication Data
US 2015/0252000 A1    Sep. 10, 2015

Related U.S. Application Data

(60) Provisional application No. 61/700,039, filed on Sep. 12, 2012.

(51) Int. Cl.
*C07D 209/08* (2006.01)
*C07D 209/10* (2006.01)
*A61K 31/496* (2006.01)
*C07D 405/12* (2006.01)

(52) U.S. Cl.
CPC ........... *C07D 209/10* (2013.01); *A61K 31/496* (2013.01); *C07D 209/08* (2013.01); *C07D 405/12* (2013.01)

(58) Field of Classification Search
CPC .... A61K 31/496; C07D 209/08; C07D 209/10
See application file for complete search history.

(56) References Cited

U.S. PATENT DOCUMENTS

| | | |
|---|---|---|
| 5,418,237 A | 5/1995 | Bottcher et al. |
| 5,532,241 A | 7/1996 | Bottcher et al. |
| 5,723,614 A | 3/1998 | Bathe et al. |
| 6,509,475 B1 | 1/2003 | Bathe et al. |
| 8,815,870 B2 | 8/2014 | Bottcher et al. |
| 2013/0225818 A1 | 8/2013 | Ferrari et al. |
| 2015/0087835 A1 | 3/2015 | Jayaraman et al. |
| 2015/0239871 A1 | 8/2015 | Jayaraman et al. |

FOREIGN PATENT DOCUMENTS

| | | | |
|---|---|---|---|
| CN | 102180868 A | 9/2011 | |
| CN | 102267932 A | 12/2011 | |
| CN | 102267985 A | 12/2011 | |
| CN | 102617558 A | 8/2012 | |
| CN | 102659660 A | 9/2012 | |
| CN | 102690224 A | 9/2012 | |
| CN | 102796037 A | 11/2012 | |
| CN | 102875440 A | 1/2013 | |
| CN | 102875538 A | 1/2013 | |
| CN | 102898346 A | 1/2013 | |
| CN | 102952121 A | 3/2013 | |
| CN | 102964287 A | 3/2013 | |
| CN | 103058912 A | 4/2013 | |
| CN | 103159749 A | 6/2013 | |
| CN | 103304466 A | 9/2013 | |
| CN | 103304526 A | 9/2013 | |
| CN | 103304547 A | 9/2013 | |
| CN | 103360373 A | 10/2013 | |
| CN | 103360374 A | 10/2013 | |
| CN | 103524498 A | 1/2014 | |
| CN | 103570697 A | 2/2014 | |
| CN | 103570698 A | 2/2014 | |
| CN | 103910668 A | 7/2014 | |
| CN | 104016972 A | 9/2014 | |
| EP | 1215210 A2 | 6/2002 | |
| WO | CN 102617558 * | 3/2012 | ........... C07D 209/08 |
| WO | 2013153492 A2 | 10/2013 | |
| WO | 2013175499 A2 | 11/2013 | |

(Continued)

OTHER PUBLICATIONS

An et al., "Synthesis of Abiraterone Acetate," Huaxue Shiji (Chemical Reagents), 2013, 35(2), pp. 167-169.

Böttcher, H. et al. "Synthese von 3-[4-(1,2,3,6-Tetrahydro-4-phenyl-1-pyridyl)butyl]-5-indolcarbonsäure, eine blutdrucksenkende Verbindung mit neuartigem Wirkprinzip," Liebigs Annalen der Chemie 1988, 8, pp. 749-752.

Cheng et al. "Improved method for synthesis of vilazodone hydrochloride," Chinese Journal of New Drugs (Zhongguo Xinyao Zazhi), 2013, vol. 22, No. 2, pp. 226-229.

Heinrich, T. et al., "Synthesis and Structure-Activity Relationship in a Class of Indolebutylpiperazines as Dual 5HT1A Receptor Agonist and Serotonin Reuptake Inhibitors," J. Med. Chem. 2004, 47, pp. 4684-4692.

Heinrich, T. et al., "Allosteric IGF-1R Inhibitors," ACS Med. Chem. Lett. 2010, 1, pp. 199-203.

(Continued)

*Primary Examiner* — Erich A Leeser

(74) *Attorney, Agent, or Firm* — The Webb Law Firm

(57) ABSTRACT

This invention provides processes for preparation of 3-alkyl indoles of Formula 1: wherein $A^1$, $A^2$ and $A^3$ are independently selected from the group consisting of: H, X, $OR^1$, CN, $CONR^2_2$ and $CO_2R^3$; $R^1$ is $C_1$-$C_6$ alkyl; $R^2$ is H or $C_1$-$C_6$ alkyl; $R^3$ is $C_1$-$C_6$ alkyl; LG is a leaving group; X is a halogen; and n is 1, 2 or 3.

16 Claims, No Drawings

(56) References Cited

FOREIGN PATENT DOCUMENTS

| WO | 2013182946 A2 | 12/2013 |
|----|---------------|---------|
| WO | 2014005134 A2 | 1/2014  |
| WO | 2014006637 A2 | 1/2014  |
| WO | 2014012505 A1 | 1/2014  |
| WO | 2014049612 A2 | 4/2014  |
| WO | 2014087428 A1 | 6/2014  |

OTHER PUBLICATIONS

Hu, B. et al., "Scale-Up Synthesis of Antidepressant Drug Vilazodone," Org. Process Res. Dev. 2012, 16, pp. 1552-1557.
Toshimitsu et al., "Indium-catalyzed reductive bromination of carboxylic acids leading to alkyl bromides," Organic Letters, vol. 14, No. 18, pp. 4842-4845 (2012).
Wenkert, E. et al., "Synthesis of Prenylated Indoles," J. Org. Chem. 1986, 51, pp. 2343-2351.
Material Safety Data Sheet (MSDS) for Isobutylaluminum Dichloride 97%, Product No. 404608, Cas No. 1888-87-5, Sigma Aldrich, Date Updated: Mar. 23, 2007, Date Printed: Jun. 9, 2016, Version 1.5.

\* cited by examiner

PROCESSES FOR THE PREPARATION OF 3-ALKYL INDOLES

TECHNICAL FIELD

The present invention relates to the synthesis of 3-alkyl indoles, which compounds are useful as intermediates in the synthesis of medicaments such as Vilazodone.

BACKGROUND

Vilazodone (2) is marketed in the United States as Viibryd™ and is indicated for the treatment of major depressive disorder.

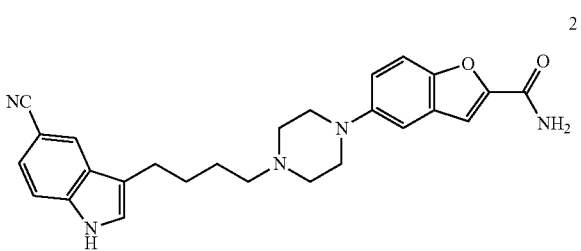 [SMILES: N#Cc1ccc2[nH]cc(CCCCN3CCN(c4ccc5oc(C(N)=O)cc5c4)CC3)c2c1]

U.S. Pat. No. 5,532,241 discloses compounds that are useful as intermediates in the preparation of Vilazodone. Examples of compounds disclosed in U.S. Pat. No. 5,532,241 include piperidine and piperazine derivatives of the following Formula:

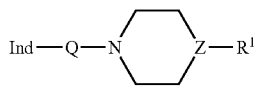

wherein Ind, Q, Z and $R^1$ are defined therein. These compounds and their physiologically acceptable salts are active on the central nervous system.

U.S. Pat. No. 5,418,237 discloses that indole derivatives of the following Formula:

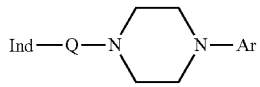

wherein Ind, Q and Ar are as defined therein, and their salts, are active on the central nervous system.

U.S. Pat. No. 6,509,475 discloses a process for the preparation of a compound of the following Formula:

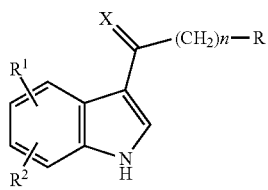

or a salt thereof in a Friedel-Crafts acylation catalyzed by a Lewis acid metal halide.

Heinrich, T., et al. in *J. Med. Chem.* 2004, 47, 4684-4692 disclose synthesis and structure-activity relationships in a class of indolebutylpiperazines as dual 5-$HT_{1A}$ receptor agonists and serotonin reuptake inhibitors. Further disclosed is that systematic structural modifications of indolealkylphenylpiperazines led to improved selectivity and affinity within this class of 5-$HT_{1A}$ receptor agonists. Introduction of electron-withdrawing groups in position 5 on the indole raises serotonin transporter affinity, and the cyano group proved to be the best substituent here. 5-Fluoro and 5-cyano substituted indoles show comparable results in in vitro and in vivo tests, and bioisosterism between these substituents was supported by calculation of the molecular electrostatic potentials and dipole moments. Compounds showing promising in vitro data were further examined in ex vivo (p-chloroamphetamine assay) and in vivo (ultrasonic vocalization) tests. Optimization of the arylpiperazine moiety indicated that the 5-benzofuranyl-2-carboxamide was best suited to increase 5-HT transporter and 5-$HT_{1A}$ receptor affinity and to suppress $D_2$ receptor binding. 5-{4-[4-(5-Cyano-3-indolyl)butyl]-1-piperazinyl}benzofuran-2-carboxamide 29 (vilazodone, EMD 68843) was identified as a highly selective 5-$HT_{1A}$ receptor agonist [GTPγS, $ED_{50}$=1.1 nM] with subnanomolar 5-$HT_{1A}$ affinity [$IC_{50}$=0.2 nM] and as a subnanomolar 5-HT reuptake inhibitor [RUI=0.5 nM] showing a great selectivity to other GPCRs (e.g., $D_2$, $IC_{50}$=666 nM).

Heinrich, T., et al. in *ACS Med. Chem. Lett.* 2010, 1, 199-203 disclose allosteric IGF-1R inhibitors. Further disclosed is that targeting allosteric protein sites is a promising approach to interfere selectively with cellular signaling cascades. The authors discovered a novel class of allosteric insulin-like growth factor-I receptor (IGF-1R) inhibitors. 3-Cyano-1H-indole-7-carboxylic acid {1-[4-(5-cyano-1H-indol-3-yl)butyl]piperidin-4-yl}amide (10) was found with nanomolar biochemical, micromolar, cellular IGF-1R activity and no relevant interference with cellular insulin receptor signaling up to 30 μM. The allosteric binding site was characterized by X-ray crystallographic studies, and the structural information was used to explain the unique mode of action of this new class of inhibitors.

Bottcher, H., et al. in *Liebigs Annalen der Chemie* 1988, 8, 749-752 disclose synthesis of 3-[4-(1,2,3,6-Tetrahydro-4-phenyl-1-pyridyl)butyl]-5-indolecarboxylic Acid, an Antihypertensive Agent with a Novel Mode of Action. Further disclosed is that the racemic drug chlormezanone is resolved into the enantiomers by HPLC on cellulose triacetate and a silica gel-bound phenylalanine polymer. By preparative column chromatography on cellulose triacetate, both enantiomers were obtained on gram scale. Their racemization rate was determined as a function of the pH value. Furthermore, on cellulose triacetate and on particular polyamides, structure analogues of chlormezanone were separated into enantiomers, some of them completely.

Wenkert, E., et al. in *J. Org. Chem.* 1986, 51, 2343-2351 disclose a synthesis of prenylated indoles. Further disclosed is that interaction of magnesium indolates and allyl oxides in the presence of bis(triphenylphosphine)nickel dichloride results in indole β-allylation, except in cases involving highly substituted indoles and allyl alcohols. This method permits the β-prenylation of indole and α-prenylation of ketones (by way of their magnesium enaminates). Base-induced interaction of ethynyldimethylcarbinyl chloride and indole under a variety of conditions yields β(β,β-dimethylvinyl)quinolone as well as variously dehydroprenylated indoles. α-Lithiation of N-(benzenesulfonyl) indole followed by treatment with prenyl bromide or β,β-dimethyl acrylyl chloride produces α-prenyl or α-oxoprenylindole derivatives, the sodium amalgam reduction of the former of which yields α-prenylindole, prenylindole and β-oxoprenylindole, the latter also being the product of the reaction of magnesium indolate and the acid chloride. Lithium aluminum hydride reduction of 1-(benzenesulfonyl)-3-oxoprenylindole affords an alcohol, whose base hydrolysis produces β-dehydroprenylindole, a compound whose dimerization has led previously to naturally occurring yuehchukene.

CN102267932 provides a process for preparation of a compound of the following formula:

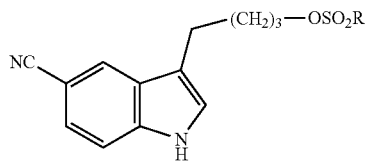

wherein R is $C_1$-$C_4$ alkyl, Ph, p-Me Ph, or $C_1$-$C_4$ alkyl Ph. The invention further relates to the application of the compound above as key intermediate for preparing Vilazodone or its pharmaceutically acceptable salt.

CN102267985 discloses a preparation method for Vilazodone and hydrochloride thereof. The method comprises the following steps: reacting the following compound:

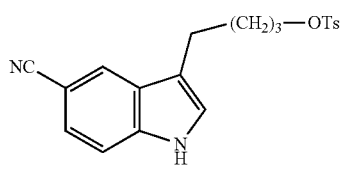

with a compound of formula:

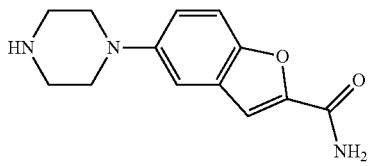

in a solvent under action of alkaline substances and collecting Vilazodone as described in the following formula:

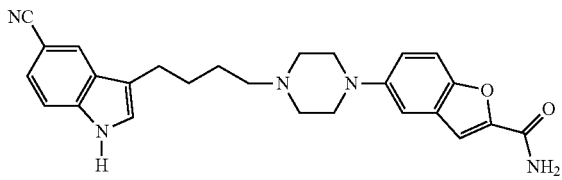 [SMILES: N#Cc1ccc2[nH]cc(CCCCN3CCN(c4ccc5oc(C(N)=O)cc5c4)CC3)c2c1]

from resultants; reacting the obtained Vilazodone with hydrochloric acid in a solvent for salt formation so as to prepare Vilazodone hydrochloride as described in the following formula:

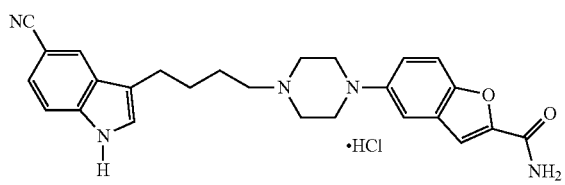 [SMILES: N#Cc1ccc2[nH]cc(CCCCN3CCN(c4ccc5oc(C(N)=O)cc5c4)CC3)c2c1 ; Cl]

CN102690224 discloses a new method for preparing 3-(4-chlorobutyl)-1H-5-cyanoindole as a Vilazodone intermediate, comprising the following steps: step (1), a compound of the following formula:

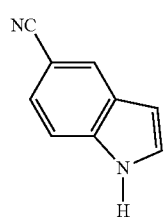

is reacted with a compound of formula:

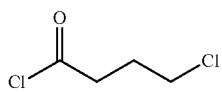

in the presence of an acylation catalyst in an organic solvent to form a compound of formula:

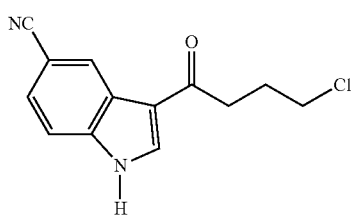

step (2), the compound above formed in step (1) is subjected to carbonyl reduction reaction in the presence of a reducing catalyst in the organic solvent.

CN102659660 relates to a preparation method and application of 3-(4-chlorobutyl)-5-cyano-1H-indole. The preparation method comprises the following steps: after dissolving 3-(4-chlorobutyryl)-5-cyano-1H-indole in a solvent, adding trifluoroacetic acid, adding sodium borohydride in batches, and treating the reaction liquid to obtain the 3-(4-chlorobutyl)-5-cyano-1H-indole.

CN102617558 provides a preparation method of Vilazodone, which comprises the following steps: reacting 5-cyanoindole, which is used as the initial raw material, with substituted phenylsulfonyl chloride under alkaline conditions, carrying out Friedel-Crafts reaction under the catalytic action of Lewis acid, reducing the product, and carrying out substitution reaction with 5-(1-piperazino)-benzofuryl-2-formamide to obtain the Vilazodone. The invention also provides three intermediate compounds related to the vilazodone preparation method.

CN102875440 discloses a preparation method of 3-(4-chlorobutyl)-5-cyanoindole which is shown as the following formula:

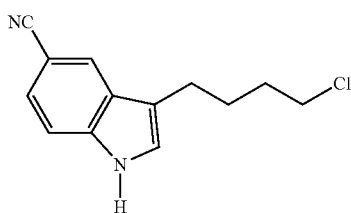 [SMILES: N#Cc1ccc2[nH]cc(CCCCCl)c2c1]

The preparation method comprises the steps as follows: carrying out following carbonyl reduction reaction on the following compound:

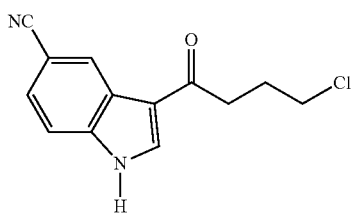 [SMILES: N#Cc1ccc2[nH]cc(C(=O)CCCCl)c2c1]

and a hydroboron reducing agent in the solvent under the catalyzing of Lewis acid to obtain the product, wherein Lewis acid is one or more of aluminium trichloride, magnesium chloride, zinc chloride and ferric chloride; and the hydroboron reducing agent is one or more of sodium borohydride, potassium borohydride, lithium borohydride and borane.

CN102875538 relates to a method for preparing 5-(4-[4-(5-cyan-3-indolyl)-butyl]-1-piperazinyl)benzofuran-2-formamide (Vilazodone) or hydrochloride thereof. The method comprises the following steps of: performing reaction between a compound of the following formula:

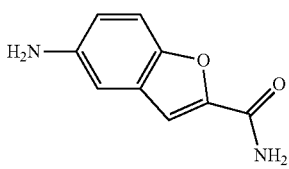 [SMILES: NC(=O)c1cc2cc(N)ccc2o1]

and a compound of the following formula:

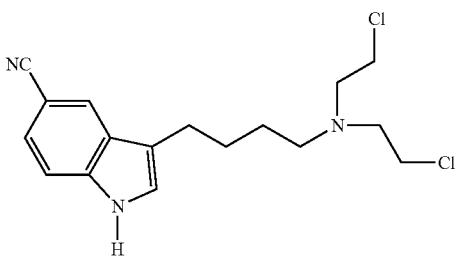 [SMILES: N#Cc1ccc2[nH]cc(CCCCN(CCCl)CCCl)c2c1]

in a solvent under the action of alkaline matter, and separating and purifying products to obtain Vilazodone; and salifying the Vilazodone and hydrochloric acid in the solvent to prepare Vilazodone hydrochloride. The invention also relates to a method for preparing the indole compound above.

CN102796037 relates to the field of chemical synthesis of medicines, particularly a 3-(4-(4-substituted-piperazino)-1-butyryl)indolyl-5-formonitrile and a preparation method thereof, and application of the compound for preparing an intermediate 3-(4-piperazino-1-yl-butyl)indolyl-5-formonitrile for synthesizing Vilazodone.

CN103058912 relates to a preparation method of 3-(4-chlorobutyl)indole-5-formonitrile. CN103058912 further teaches (4-chlorobutyl)indole-5-formonitrile is an important intermediate for synthesis of vilazodone hydrochloride. 5-Cyanoindole and 4-chlorobutyryl chloride as raw materials undergo a Friedel-Crafts acylation reaction and then the product is reduced by sodium borohydride/trifluoroacetic acid into 3-(4-chlorobutyl)indole-5-formonitrile.

Hu, B., et al. in *Org. Process Res. Dev.* 2012, 16, 1552-1557 disclose a scale-up synthesis of antidepressant drug Vilazodone. A scale-up synthesis of antidepressant drug vilazodone was accomplished in five steps. Friedel-Crafts acylation of 1-tosyl-1H-indole-5-carbonitrile with 4-chlorobutyryl chloride, selective deoxygenation in $NaBH_4/CF_3COOH$ system coupled with ethyl 5-(piperazin-1-yl)-benzofuran-2-carboxylate hydrochloride, one-step deprotection and esterolysis, and the final ammonolysis led to the target molecule vilazodone in 52.4% overall yield and 99.7% purity.

SUMMARY

Methods of the present invention may provide compounds of Formula 1

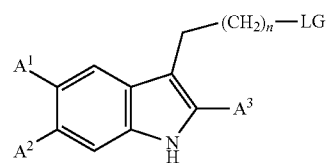

in good yield and purity despite the presence of one or more sensitive functional groups such as cyano and chloro. Methods of the present invention may also provide the use of nearly stoichiometric quantities of economical, safe and easy to handle reagents and a product that may be easily isolatable.

Illustrative embodiments of the present invention provide a process for the preparation of a compound of Formula 1:

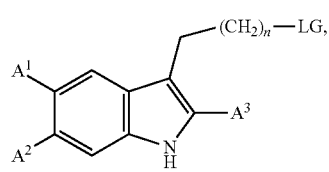

the process comprising reducing a compound of Formula 3:

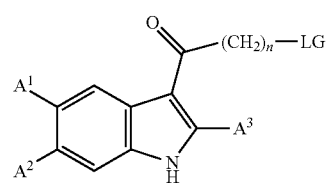

in the presence of either (i) sodium borohydride and $MCl_3$, or (ii) indium bromide and a compound of Formula 4:

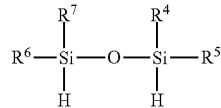

wherein $A^1$, $A^2$ and $A^3$ are independently selected from the group consisting of: H, X, $OR^1$, CN, $CONR^2_2$ and $CO_2R^3$; $R^1$ is $C_1$-$C_6$ alkyl; $R^2$ is H or $C_1$-$C_6$ alkyl; $R^3$ is $C_1$-$C_6$ alkyl; $R^4$ is $C_1$-$C_6$ alkyl; $R^5$ is $C_1$-$C_6$ alkyl; $R^6$ is $C_1$-$C_6$ alkyl; $R^7$ is $C_1$-$C_6$ alkyl; LG is a leaving group; X is a halogen; n is 1, 2 or 3; and M is aluminum or iron.

Illustrative embodiments of the present invention provide a process described herein wherein $A^1$ is selected from the group consisting of: X, CN, $CONR^2_2$ and $CO_2R^3$; $A^2$ is selected from the group consisting of: H, X, $CONR^2_2$ and $CO_2R^3$; $A^3$ is selected from the group consisting of: H, X, $CONR^2_2$ and $CO_2R^3$; LG, is selected from the group consisting of: a halogen or a sulfonyloxy group; and n is 3.

Illustrative embodiments of the present invention provide a process described herein wherein $A^1$ is selected from the group consisting of: X, CN and $CONR^2_2$; $A^2$ is selected from the group consisting of: H, X, and $CONR^2_2$; $A^3$ is selected from the group consisting of: H, X, and $CONR^2_2$; LG is chloro, bromo or iodo; and $R^2$ is H.

Illustrative embodiments of the present invention provide a process described herein wherein $A^1$ is CN; and $A^2$ and $A^3$ are H.

Illustrative embodiments of the present invention provide a process described herein wherein LG is chloro.

Illustrative embodiments of the present invention provide a process described herein wherein the reducing occurs in the presence of sodium borohydride and $MCl_3$ and M is aluminum.

Illustrative embodiments of the present invention provide a process described herein wherein the reducing occurs in the presence of sodium borohydride and $MCl_3$ and M is iron.

Illustrative embodiments of the present invention provide a process described herein wherein the reducing occurs in the presence of indium bromide and a compound of Formula 4 and $R^4$ is methyl, $R^5$ is methyl, $R^6$ is methyl and $R^7$ is methyl.

Illustrative embodiments of the present invention provide a process described herein wherein the reducing is conducted in a solvent selected from the group consisting of nitriles, esters and ethers.

Illustrative embodiments of the present invention provide a process described herein wherein the reducing is conducted in tetrahydrofuran.

Illustrative embodiments of the present invention provide a process described herein wherein the reducing occurs in the presence of indium bromide and the compound of Formula 4 and the compound of Formula 4 is 1,1,3,3-tetramethyldisiloxane.

Illustrative embodiments of the present invention provide a process described herein wherein the reducing is conducted in toluene.

Illustrative embodiments of the present invention provide a process described herein further comprising crystallizing the compound of Formula 1 using a solvent selected from the group consisting of: n-BuOH, toluene, methanol, isopropyl alcohol and mixtures of acetonitrile and water.

Illustrative embodiments of the present invention provide a process described herein further comprising crystallizing the compound of Formula 1 using n-BuOH.

Illustrative embodiments of the present invention provide a process described herein further comprising crystallizing the compound of Formula 1 using toluene.

Illustrative embodiments of the present invention provide a process described herein further comprising crystallizing the compound of Formula 1 using methanol.

Illustrative embodiments of the present invention provide a process described herein further comprising converting the compound of Formula 1 to Vilazodone.

Illustrative embodiments of the present invention provide a composition comprising Vilazodone and iron.

Other aspects and features of the present invention will become apparent to those ordinarily skilled in the art upon review of the following detailed description of specific embodiments of the invention.

DETAILED DESCRIPTION

As used herein, the term "alkyl" by itself or as part of another substituent, means, unless otherwise stated, a straight or branched chain, hydrocarbon radical, having the number of carbon atoms designated (e.g. $C_1$-$C_{10}$ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl and the like.

As used herein the term "leaving group" refers to a halogen atom (e.g. chlorine, bromine and iodine) and/or sulfonyloxy groups (e.g. methanesulfonyloxy, trifluoromethanesulfonyloxy, and p-toluenesulfonyloxy).

Illustrative processes of the present invention provide compounds of Formula 1 as a final product. Compounds of Formula 1 include:

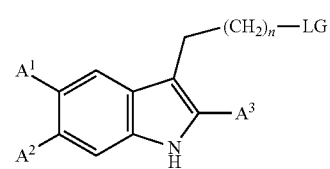

wherein
$A^1$ is selected from the group consisting of: H, X, $OR^1$, CN, $CONR^2_2$ and $CO_2R^3$;
$A^2$ is selected from the group consisting of: H, X, $OR^1$, CN, $CONR^2_2$ and $CO_2R^3$;
$A^3$ is selected from the group consisting of: H, X, $OR^1$, CN, $CONR^2_2$ and $CO_2R^3$;
$R^1$ is $C_1$-$C_6$ alkyl;
$R^2$ is H or $C_1$-$C_6$ alkyl;
$R^3$ is $C_1$-$C_6$ alkyl;
LG is a leaving group;
X is a halogen; and
n is 1, 2 or 3.

In particular embodiments of the present invention, $A^1$ is selected from the group consisting of X, CN, $CONR^2_2$ and $CO_2R^3$. In particular embodiments, $A^1$ is selected from the group consisting of: X, CN and $CONR^2_2$, wherein $R^2$ is H. In particular embodiments of the present invention, $A^1$ is CN.

In particular embodiments of the present invention, $A^2$ is selected from the group consisting of H, X, $CONR^2_2$ and $CO_2R^3$. In particular embodiments, $A^2$ is selected from the group consisting of: H, X, and $CONR^2_2$, wherein $R^2$ is H. In particular embodiments of the present invention, $A^2$ is H.

In particular embodiments of the present invention, $A^3$ is selected from the group consisting of H, X, $CONR^2_2$ and $CO_2R^3$. In particular embodiments, $A^3$ is selected from the group consisting of: H, X, and $CONR^2_2$, wherein $R^2$ is H. In particular embodiments of the present invention, $A^3$ is H.

The leaving group, LG, may be a halogen or a sulfonyloxy group. Often LG is chloro, bromo or iodo. LG is often chloro.

In particular embodiments of the present invention, n is 3.

Provided herein are processes for the preparation of a compound of Formula 1. The processes of the present invention comprise reducing a compound of Formula 3:

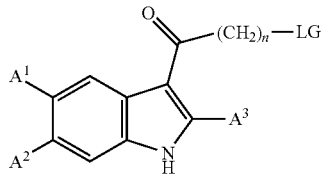

in the presence of either (i) sodium borohydride and $MCl_3$, or (ii) indium bromide and a compound of Formula 4:

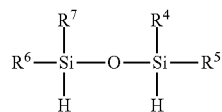

wherein
$A^1$, $A^2$ and $A^3$ are independently selected from the group consisting of: H, X, $OR^1$, CN, $CONR^2_2$ and $CO_2R^3$;
$R^1$ is $C_1$-$C_6$ alkyl;
$R^2$ is H or $C_1$-$C_6$ alkyl;
$R^3$ is $C_1$-$C_6$ alkyl;
$R^4$ is $C_1$-$C_6$ alkyl;
$R^5$ is $C_1$-$C_6$ alkyl;
$R^6$ is $C_1$-$C_6$ alkyl;
$R^7$ is $C_1$-$C_6$ alkyl;
LG is a leaving group;
X is a halogen;
n is 1, 2 or 3; and
M is aluminum or iron.

In illustrative embodiments, processes of the present invention may comprise reducing, in the presence of sodium borohydride and $MCl_3$, a compound of Formula 3:

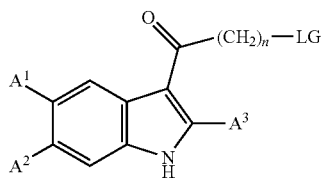

wherein $A^1$, $A^2$, $A^3$, LG and n are as defined above for Formula 1, and M is aluminum or iron. Often M is aluminum. Often M is iron.

Reducing the compound of Formula 3 may be conducted in a suitable non-reactive solvent. Suitable solvents are solvents in which a compound of Formula 3 is soluble. Examples of suitable solvents are nitriles (such as acetonitrile), esters (such as ethyl acetate) and ethers (such as tetrahydrofuran). Often, the solvent is tetrahydrofuran (THF). Optimization of reaction yield and purity may be necessary, depending on the choice of solvent and the structure of the compound of Formula 3.

In reducing the compound of Formula 3, the reactants and reagents may be added in any order. The reduction may be conducted at a suitable temperature depending upon the conditions and may vary from about 0° C. to about the boiling point of the solvent. Often, the reduction is conducted at from about 30° C. to about 45° C. Following the quench, phase separation may be assisted by filtering the reaction mixture through a suitable medium such as Celite™.

After reducing the compound of Formula 3 to the compound of Formula 1, the compound of Formula 1 may be isolated by crystallization. The crystallization may be conducted in a suitable solvent selected from the group consisting of toluene, methanol, isopropyl alcohol and mixtures of acetonitrile/water. Often the compound of Formula 1 is crystallized from toluene or methanol. Often the compound of Formula 1 is crystallized from toluene. Often the compound of Formula 1 is crystallized from methanol.

Illustrative embodiments of the present invention also include processes for the preparation of a compound of Formula 1a. Illustrative embodiments of the present invention provide a process for the preparation of a compound of Formula 1a:

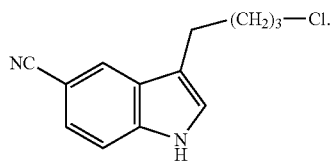

The processes may comprise reducing a compound of Formula 3a:

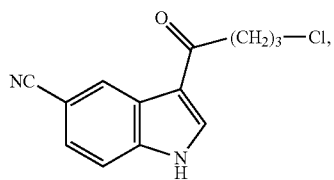

in the presence of $InBr_3$ and a compound of Formula 4:

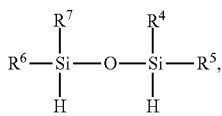

wherein $R^4$, $R^5$, $R^6$, and $R^7$, are each independently selected from the group of: $C_1$-$C_6$ alkyl.

Methods employing a compound of Formula 4 and InBr$_3$ described herein may be used to reduce a compound of Formula 3a despite the presence of sensitive groups such as alkyl chloride and indole, which are prone to reduction.

In a particular embodiment, $R^4$, $R^5$, $R^6$, and $R^7$, are each methyl, thereby making the compound of Formula 4: 1,1,3,3-tetramethyldisiloxane.

Reducing the compound of Formula 3a may be conducted in a suitable non-reactive solvent, for example, ethers (such as THF) and aromatic hydrocarbons. Toluene is an example of a suitable solvent.

In reducing the compound of Formula 3a, a suitable molar amount of disiloxane may be used, for example, from about 1 equivalent to about 3 equivalents with respect to the compound of Formula 3a. If desired, more than 1 molar equivalent of disiloxane may be used to facilitate stirring of the reaction mass. The reaction may be performed at a suitable temperature, for example, from about 25° C. to about the boiling point of the solvent. Often, the reaction is performed at a temperature of from about 45° C. to about 70° C.

Inorganic salts may be removed by, for example, aqueous extraction, to afford a biphasic, oily residue. The product may be crystallized from a suitable solvent such as an alcohol, for example, but not limited to n-BuOH. The crystallization may be induced by seeding or cooling, if desired. Other solvents, such as toluene, methanol, isopropyl alcohol and mixtures of acetonitrile/water may also be used to crystallize the product obtained using InBr$_3$, however, the crystallization process may be improved by removing a silanol by-product.

Compounds of Formula 1, including a compound of Formula 1a, may be used in processes for the preparation of Vilazodone. There are many processes known to a person of skill in the art for converting a compound of Formula 1 to Vilazodone and any such process may be applied to compounds of Formula 1 prepared by a process of the present invention. An example of such a process is disclosed in U.S. Pat. No. 5,532,241. If a compound of Formula 1 is converted to Vilazodone and the compound of Formula 1 was prepared by a process described herein in which M is iron, then it is possible that iron may be present in the final Vilazodone product.

EXAMPLES

The following examples are illustrative of some of the embodiments of the invention described herein. These examples do not limit the spirit or scope of the invention in any way.

Example 1

To a suspension of 3-(4-chlorobutyryl)-1H-indole-5-carbonitrile (20 g, 0.081 mol) in THF (120 mL) was charged FeCl$_3$ (13.2 g, 0.081 mol). The mixture was then stirred for about 30 minutes followed by portion wise addition of NaBH$_4$ (3.4 g, 0.089 mol) while controlling the internal temperature to between 30-50° C. Reaction completion was monitored by TLC. After reaction completion, water was added to quench the reaction, followed by extraction and crystallization from toluene to afford 3-(4-chlorobutyl)-1H-indole-5-carbonitrile (1) as a crystalline solid in 70% yield.

Example 2

To a cooled (0-5° C.) suspension of 3-(4-chlorobutyryl)-1H-indole-5-carbonitrile (100 g, 0.405 mol) in THF (600 mL) was charged FeCl$_3$ (65.8 g, 0.405 mol) portion wise while maintaining the temperature below 20° C. The mixture was cooled to 0-5° C. followed by portion wise addition of NaBH$_4$ (16.9 g, 0.446 mol) while maintaining the temperature below 20° C. The mixture was then heated to 35-40° C. and maintained until reaction completion by TLC. After reaction completion, toluene (500 mL) was charged and the mixture was cooled to 0-5° C. before quenching with water (400 mL). Following Celite™ addition (10 wt %), the mixture was filtered through a Celite™ pad and the phases were separated. The organic phase was washed with water and distilled under vacuum (3 vol). Toluene (3 vol) was charged and the distillation was repeated. The mixture was allowed to stir for 8 to 16 hours at 20-25° C., followed by cooling to 0-5° C. before isolation of the solid by filtration to afford 3-(4-chlorobutyl)-1H-indole-5-carbonitrile (1) as a crystalline solid in 69% yield.

Example 3

To a suspension of 3-(4-chlorobutyryl)-1H-indole-5-carbonitrile (5.0 g, 0.020 mol) in THF (150 mL) was charged sodium borohydride (1.15 g, 0.030 mol). The mixture was then stirred at 20-30° C. for about 20 minutes followed by portion wise addition of AlCl$_3$ (4.1 g, 0.030 mol). Reaction completion was monitored by TLC. After reaction completion, water was introduced to quench the reaction, followed by extraction and filtration through a silica pad, eluting with toluene, to afford 3-(4-Chlorobutyl)-1H-indole-5-carbonitrile (1) as a crystalline solid (69% yield).

Example 4

Crude 3-(4-chlorobutyl)-1H-indole-5-carbonitrile (65 g) was suspended in methanol (130 mL) and heated until complete dissolution. The solution was then cooled to 0-5° C. and maintained for 2-3 hours. The solid thus formed was filtered and washed twice with methanol (30 mL) to yield purified 1 in 70% yield (98% purity by HPLC).

Example 5

3-(4-Chlorobutanoyl)-1H-indole-5-carbonitrile (10.00 g, 0.0405 mol) was suspended in toluene (50 mL) at 20-25° C., followed by addition of InBr$_3$ (0.72 g, 0.0020 mol) and 1,1,3,3-tetramethyldisiloxane (10.89 g, 0.0811 mol). The mixture was then heated to 60-65° C. and maintained until reaction completion by TLC (ca. 1 hour). After reaction completion, the mixture was cooled to 20-25° C. and diluted with nBuOH (30 mL) and H$_2$O (30 mL). The mixture was washed with aqueous citric acid and then water. The phases were separated and the turbid organic phase was filtered through a pad of celite. The filtrate was concentrated under vacuum to a biphasic oily residue. The residue was diluted with nBuOH (20 mL), seeded with pure 3-(4-chlorobutyl)-1H-indole-5-carbonitrile and stirred at 20-25° C. for 3 days. The product was isolated by filtration, washed with heptanes and dried under vacuum to afford 3-(4-chlorobutyl)-1H-indole-5-carbonitrile as a crystalline solid in 51% yield and 96% purity (HPLC).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A process for the preparation of a compound of Formula 1:

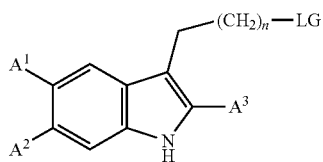

the process comprising
reducing a compound of Formula 3:

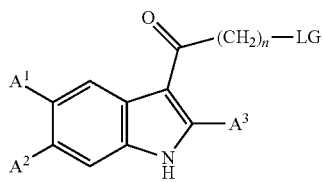

in the presence of sodium borohydride and $MCl_3$
wherein
$A^1$, $A^2$ and $A^3$ are independently selected from the group consisting of: H, X, $OR^1$, CN, $CONR^2_2$ and $CO_2R^3$;
$R^1$ is $C_1$-$C_6$ alkyl;
$R^2$ is H or $C_1$-$C_6$ alkyl;
$R^3$ is $C_1$-C6 alkyl;
LG is a leaving group;
X is a halogen;
n is 1, 2 or 3; and
M is aluminum or iron.

2. The process of claim 1 wherein
$A^1$ is selected from the group consisting of: X, CN, $CONR^2_2$ and $CO_2R^3$;
$A^2$ is selected from the group consisting of: H, X, $CONR^2_2$ and $CO_2R^3$;
$A^3$ is selected from the group consisting of: H, X, $CONR^2_2$ and $CO_2R^3$;
LG, is selected from the group consisting of: a halogen or a sulfonyloxy group; and
n is 3.

3. The process of claim 1 wherein
$A^1$ is selected from the group consisting of: X, CN and $CONR^2_2$;
$A^2$ is selected from the group consisting of: H, X, and $CONR^2_2$;
$A^3$ is selected from the group consisting of: H, X, and $CONR^2_2$;
LG is chloro, bromo or iodo; and
$R^2$ is H.

4. The process of claim 1 wherein
$A^1$ is CN; and
$A^2$ and $A^3$ are H.

5. The process of claim 1 wherein LG is chloro.

6. The process of claim 1 wherein M is aluminum.

7. The process of claim 1 wherein M is iron.

8. The process of claim 6 wherein the reducing is conducted in a solvent selected from the group consisting of nitriles, esters and ethers.

9. The process of claim 6 wherein the reducing is conducted in tetrahydrofuran.

10. The process of claim 1 further comprising crystallizing the compound of Formula 1 using a solvent selected from the group consisting of: n-BuOH, toluene, methanol, isopropyl alcohol and mixtures of acetonitrile and water.

11. The process of claim 1 further comprising crystallizing the compound of Formula 1 using n-BuOH.

12. The process of claim 1 further comprising crystallizing the compound of Formula 1 using toluene.

13. The process of claim 1 further comprising crystallizing the compound of Formula 1 using methanol.

14. The process of claim 1 further comprising converting the compound of Formula 1 to Vilazodone.

15. The process of claim 7 wherein the reducing is conducted in a solvent selected from the group consisting of nitriles, esters and ethers.

16. The process of claim 7 wherein the reducing is conducted in tetrahydrofuran.

* * * * *

UNITED STATES PATENT AND TRADEMARK OFFICE
CERTIFICATE OF CORRECTION

PATENT NO. : 9,533,949 B2
APPLICATION NO. : 14/427926
DATED : January 3, 2017
INVENTOR(S) : Craig Stewart et al.

It is certified that error appears in the above-identified patent and that said Letters Patent is hereby corrected as shown below:

In the Claims

Column 13, Line 50, Claim 1, delete "$C_1$-C6" and insert -- $C_1$-$C_6$ --

Signed and Sealed this
Twelfth Day of September, 2017

Joseph Matal
*Performing the Functions and Duties of the
Under Secretary of Commerce for Intellectual Property and
Director of the United States Patent and Trademark Office*